(12) United States Patent
Chambon et al.

(10) Patent No.: US 7,504,836 B2
(45) Date of Patent: Mar. 17, 2009

(54) DEVICE FOR MEASURING THE QUALITY AND/OR DEGRADATION OF A FLUID, PARTICULARLY A FOOD OIL

(75) Inventors: Gérald Chambon, Av. du Grey 51, 1018 Lausanne (CH) 1018; Martin Gijs, Ecublens (CH)

(73) Assignees: Ecole Polytechnique Federale de Lausanne, Lousanne (CH); Gerald Chambon, Lausanne (CH)

( * ) Notice: Subject to any disclaimer, the term of this patent is extended or adjusted under 35 U.S.C. 154(b) by 40 days.

(21) Appl. No.: 10/542,636

(22) PCT Filed: Dec. 30, 2003

(86) PCT No.: PCT/EP03/14955

§ 371 (c)(1),
(2), (4) Date: Jul. 19, 2005

(87) PCT Pub. No.: WO2004/065957

PCT Pub. Date: Aug. 5, 2004

(65) Prior Publication Data

US 2006/0288877 A1   Dec. 28, 2006

(30) Foreign Application Priority Data

Jan. 20, 2003  (EP) .................................. 03075203

(51) Int. Cl.
*G01R 27/08* (2006.01)
*G01R 27/26* (2006.01)

(52) U.S. Cl. ...................................... 324/698; 324/686

(58) Field of Classification Search ................. 324/686, 324/658, 649, 600, 698, 663, 690, 659, 664, 324/665, 672, 679; 73/61.41; 340/603, 631
See application file for complete search history.

(56) References Cited

U.S. PATENT DOCUMENTS

| 4,728,882 A | 3/1988 | Stanbro et al. |
| 4,733,556 A | 3/1988 | Meitzler et al. |
| 5,111,221 A | 5/1992 | Fare et al. |
| 5,262,732 A * | 11/1993 | Dickert et al. ............... 324/672 |

(Continued)

FOREIGN PATENT DOCUMENTS

DE   196 49 366 A1   6/1998

(Continued)

*Primary Examiner*—Diego Gutierrez
*Assistant Examiner*—Hoai-An D Nguyen
(74) *Attorney, Agent, or Firm*—Sughrue Mion, PLLC

(57) ABSTRACT

The invention relates to a device for measuring the quality and/or degradation of a fluid, especially an oil, comprising a sensor consisting of at least one pair of electrodes which are distanced from each other. Said sensor is immersed in the fluid which is to be measured. The electrodes and the fluid form a capacitive element whose capacity varies according to the dielectric constant of the fluid. The sensor can provide an electric output signal representing said dielectric constant. The inventive device also comprises processing means which receive the output signal and which can determine the degree of quality and/or degradation of the fluid on the basis of said output signal. The invention is characterized in that the electrodes extend substantially on the same plane and in that the fluid surrounds the two surfaces of the electrodes on both sides of said plane.

2 Claims, 7 Drawing Sheets

U.S. PATENT DOCUMENTS

| | | |
|---|---|---|
| 5,818,731 A | 10/1998 | Mittal et al. |
| 6,204,656 B1 * | 3/2001 | Cheiky-Zelina et al. .... 324/71.4 |
| 6,293,142 B1 * | 9/2001 | Pchelnikov et al. ....... 73/290 R |
| 6,433,560 B1 * | 8/2002 | Hansen et al. .............. 324/668 |
| 6,459,995 B1 * | 10/2002 | Collister ..................... 702/23 |
| 6,469,521 B1 | 10/2002 | Klun |
| 6,600,306 B1 * | 7/2003 | Pernot et al. ............... 324/71.1 |
| 6,718,819 B2 * | 4/2004 | Schoess .................... 73/53.05 |
| 6,822,461 B2 * | 11/2004 | Klun .......................... 324/698 |
| 6,888,358 B2 * | 5/2005 | Lechner et al. ............. 324/607 |
| 7,129,715 B2 * | 10/2006 | Hayashi et al. ............. 324/685 |

FOREIGN PATENT DOCUMENTS

| | | |
|---|---|---|
| GB | 2 136 130 | 9/1984 |
| WO | WO 00/62057 A1 | 10/2000 |

\* cited by examiner

DEVICE FOR MEASURING THE QUALITY AND/OR DEGRADATION OF A FLUID, PARTICULARLY A FOOD OIL

BACKGROUND OF THE INVENTION

The present invention concerns a capacitive device for measuring the quality and/or degradation of a fluid, particularly an oil. The invention concerns in particular a device of this type for measuring the quality and/or degradation of a food oil, such as frying oil, directly in the cooking apparatus.

It is well known that food oils deteriorate during cooking, particularly when they are repeatedly brought to high temperatures. Typically, in order to fry food, these oils are brought to temperatures of the order of 180° C. At such temperatures a multitude of chemical reactions occur, such as polymerisations, thermo-oxidisations etc, which significantly alter the quality of the oil. The quantity of certain products of these reactions must not exceed a threshold imposed by law, since beyond such thresholds the oil is considered unfit for consumption. It is thus important to be able to detect the threshold in a reliable way in order to replace the oil as soon as it is necessary to do so. For a long time determination of the threshold was left to the cooks, who, after a visual or olfactory inspection, determined whether the oil was still fit for consumption. Of course, such a method is purely subjective and is consequently unreliable.

Various devices have been proposed in the prior art until now to try to overcome this problem in order to be able to measure objectively the quality and/or degradation of food oils. Since the degradation of food oils results in particular from the thermo-oxidisation thereof and this reaction produces polar compounds, devices have been envisaged in which the degree of degradation of the oil has been correlated with the dielectric constant of the oil, by measuring the capacitance of a capacitor in which the oil to be monitored forms the dielectric.

Such a device is disclosed for example in U.S. Pat. No. 5,818,731. This document discloses a device for measuring the quality of food oils to be mounted in a cooking apparatus such as a deep fryer. This device simultaneously monitors variations in the capacitance and optical transmission of the oil within the cooking or frying temperature range. The capacitive measuring unit comprises two sets of parallel plates interlaced with each other to define a measuring capacitor. When the sets of plates are immersed in oil, the latter forms the dielectric of the measuring capacitor for said unit and the variation in capacitance is measured by means of a direct current oscillator bridge circuit. However, this device has several drawbacks. A first drawback lies in the fact that the spaces been the plates are small and that, when the plates are plunged into the oil, the latter does not flow easily between the plates because of capillary phenomena. A regular change of the oil present between the plates is not, therefore guaranteed, which can lead to erroneous oil degradation measurement results. Moreover, solid particles present in the oil can also get caught between the plates, which has a negative effect on the measured signal. It should also be noted that, given the small space between the plates, the configuration of the capacitor in parallel plates does not allow easy access to these spaces, which makes it complex to carry out maintenance operations on the device. Another drawback lies in the fact that the capacitor with plates is bulky and occupies a significant amount of space on the cooking apparatus. Moreover, the single measuring sensor formed by the capacitor is subject to temperature variations, which can lead to erroneous capacitance measurements, such that the device has to provide means for compensating for such errors. The solution proposed in this document consists in using a temperature sensor that provides an indication to a suitable processing circuit to take account of temperature variations measured by software means integrating data relating to the oil to be monitored. Consequently, if the quality of the oil changes or if new oil is used, the software means have to be updated which makes the device inflexible to use.

SUMMARY OF THE INVENTION

It is a main object of the present invention to overcome the drawbacks of the aforementioned prior art by providing an improved device for measuring the quality and/or degradation of a fluid by a capacitive measurement, having a simple, compact and inexpensive structure.

It is also an object of the present invention to provide a device of this type wherein the capacitive measuring sensor has a structure facilitating the flow of the fluid to be measured in proximity to its electrodes while maintaining a high level of capacitance variation measuring sensitivity.

It is also an object of the present invention to provide a device of this type in which the probability of particles present in the fluid becoming caught between the electrodes of the measuring capacitor is reduced.

It is another object of the present invention to provide a device of this type, wherein maintenance and particularly the cleaning of the measuring sensor, is facilitated.

It is another object of the present invention to provide a device of this type wherein the capacitance measurement is no longer temperature dependent, while maintaining great flexibility of use, i.e. a device whose processing circuit software means do not require systematic updating when one wishes to use the device with a fluid of a different nature.

The invention therefore concerns a device for measuring the quality and/or degradation of a fluid, particularly an oil, comprising a sensor including at least one pair of electrodes spaced apart from each other, to be immersed in the fluid to be measured, the electrodes and the fluid forming a capacitive measuring element whose capacitance varies as a function of the dielectric constant of the fluid. The sensor is capable of providing an electrical output signal representative of said dielectric constant. The device further includes processing means receiving said output signal and capable of determining the degree of quality and/or degradation of the fluid on the basis of said output signal. This device is characterized in that said electrodes extend in substantially the same plane and in that the fluid bathes both surfaces of the electrodes, on either side of the said plane.

Owing to these features, the fluid to be measured can flow easily and quickly on either side of the electrodes of the capacitive measuring element. The fluid present in proximity to the electrodes can thus be constantly renewed, which improves the reliability and precision of the measurements provided by the device insofar as the latter are representative of the evolution of the quality of the fluid as a whole. This structure further greatly reduces the risk of particles becoming caught in the air gap of the capacitive element. Another advantage of the device according to the invention lies in the fact that access to the air gap is easy, which facilitates the sensor maintenance operations. It should also be noted that since the fluid bathes the surfaces of the measuring electrodes on either side of their median plane, it is possible to obtain a high level of measuring sensitivity.

According to a preferred embodiment of the invention, the sensor further includes a reference capacitive element, comprising at least one pair of reference electrodes spaced apart from each other, to be immersed in a reference fluid, the reference electrodes and fluid forming a reference capacitive element whose capacitance varies as a function of the dielectric constant of the reference fluid of the reference fluid, said reference capacitive element being capable of providing a reference signal representative of said reference dielectric constant to the processing means and the processing means being arranged to compare the output signal with the reference signal.

The reference capacitive element can thus permanently measure the dielectric properties of a "new" or in other words non-degraded reference fluid, and supply a reference dielectric constant value for the fluid, which can be compared to the dielectric constant value provided by the capacitive measuring element. The use of two sensors also removes dielectric constant variations due to temperature variations.

When the measuring device is associated with a cooking apparatus comprising a vat containing the cooking oil, the capacitive measuring element can be immersed in the oil in which the food is fried while the reference capacitive element is immersed in another reference food oil having the same features as the cooking oil, but contained in a enclosed space insulated therefrom.

Preferably, the enclosed space containing the reference food oil is in thermal contact with the cooking oil. The reference food oil can of course be renewed periodically, for example once a day or, if necessary, continuously in order to provide a well defined reference dielectric constant value for a non-degraded oil. This renewal can be performed automatically or manually.

BRIEF DESCRIPTION OF THE DRAWINGS

Other features and advantages of the present invention will appear in the following description of preferred embodiments of measuring devices according to the invention, given by way of non-limiting examples with reference to the annexed drawings, in which.

DESCRIPTION OF PREFERRED EMBODIMENTS

Figure 1:
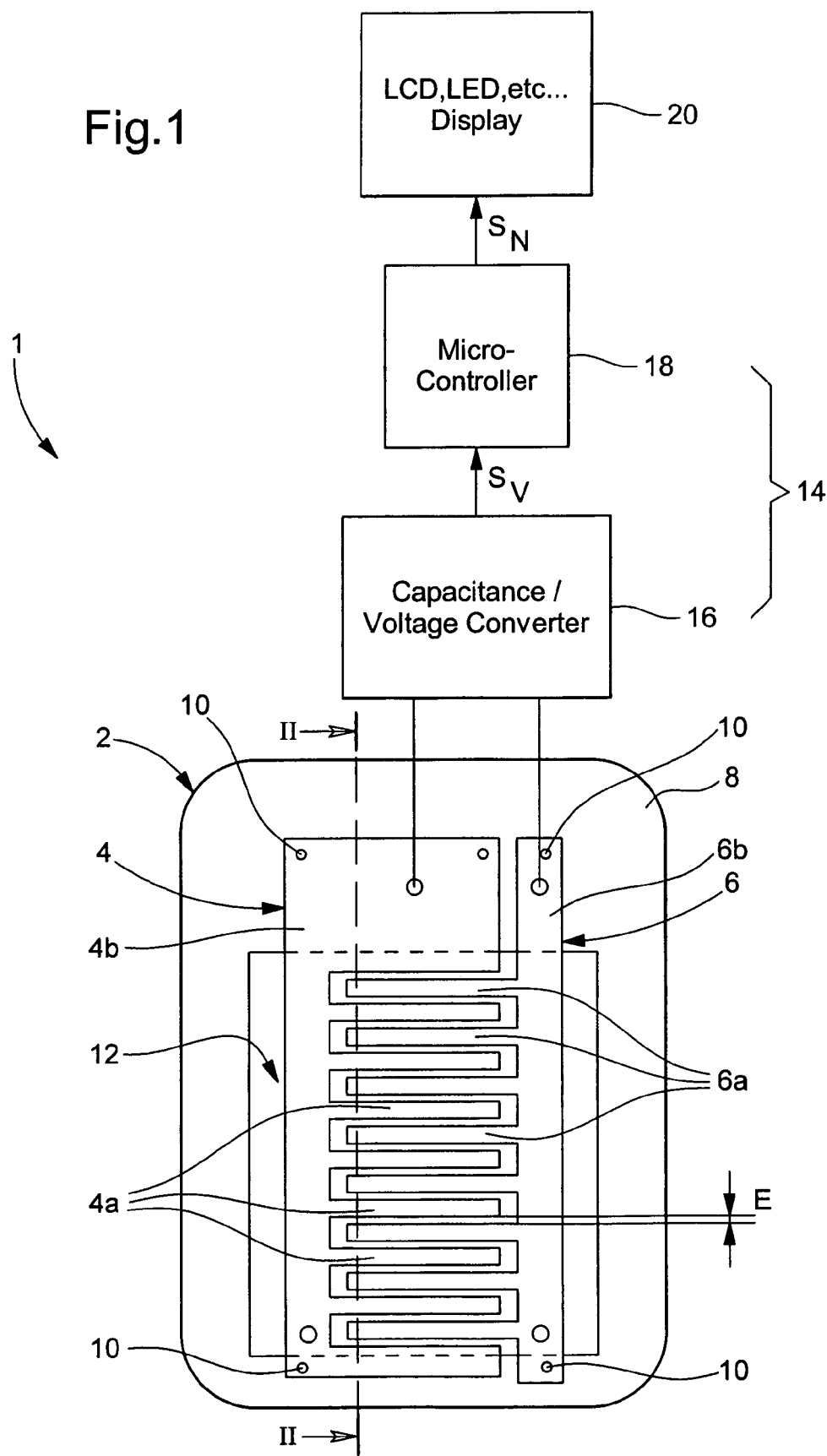
FIG. 1 is a schematic view of a first embodiment of the measuring device according to the invention.

With reference first of all to FIG. 1, there is shown a first embodiment of the capacitive device for measuring the quality and/or degradation of a fluid, particularly an oil, designated by the general reference 1.

It will be noted that the following description will be made in an application of device 1 to the measurement of the quality and/or degradation of a food oil or similar, used for frying food in cooking apparatuses comprising a vat in which the oil can be heated typically to around 200° C.

Measuring device 1 comprises a sensor 2 including a pair of electrodes 4, 6 spaced apart from each other and to be immersed in a fluid F (FIG. 2), for example the oil of a deep fryer, whose quality and/or degradation one wishes to measure to determine whether it is still fit for use. Electrodes 4, 6 form with oil F a capacitive measuring element EFM whose capacitance varies as a function of the dielectric constant of the oil. When the oil is degraded, the quantity of polar compounds present therein increases and causes an increase in its dielectric constant. Thus, by measuring the evolution of the capacitance of the capacitive measuring element EFM, the degree of quality and/or degradation of the oil can be determined. Sensor 2 and more specifically its capacitive element EFM, is thus capable of providing an electrical output signal representative of the dielectric constant of the oil over a wide temperature range, in particular between 20° C. and 200° C.

Each electrode 4, 6 of the pair has the shape of a comb having a plurality of teeth 4a, 6a substantially parallel to each other and extending from a base 4b, 6b. Electrodes 4 and 6 are arranged in relation to each other such that teeth 4a of one electrode 4 are interdigited with the teeth 6a of the other electrode 6. The teeth of electrodes 4 and are thus arranged in substantially the same plane.

It will be noted in this regard that electrodes 4 and 6 are for example formed from the same flat plate cut in a suitable manner, the plate being sufficiently rigid for the electrodes to keep their shape when they are handled. In the example described, the electrodes are made from a plate and food grade steel (18-10 carbon based austenitic steel) having a thickness comprised between 0.1 and 3 mm. Other types of food grade steel can also be used, for example Z7CN18-09, Z3CND18-12-02, Z6CNDT17-12 and Z7CNU16-04. The plate is cut by means of a laser beam, which enables air gaps to be made between the teeth of the electrodes comprised between 10 nm and 1 mm. It is clear that the smaller the air gap E, the greater the sensitivity of the capacitive element. According to an alternative embodiment, electrodes formed of a substrate coated with a conductive material, for example a substrate coated with a layer of gold, platinum or similar, could be envisaged.

In the embodiment shown, electrodes 4 and 6 are secured to an insulating substrate 8, which, in conjunction with alignment means 10, holds the electrodes in a fixed position in relation to each other. More specifically, electrodes 4 and 6 are each fixed to substrate 8 via a fixing lug extending from their base 4b, 6b, via any appropriate means, for example screws or suchlike. Alignment means 10 comprise for example positioning pins driven into substrate 8 and cooperating with holes for this purpose in electrodes 4 and 6.

Substrate 8 has the shape of a frame having a central aperture 12 arranged facing the region for measuring electrodes 4 and 6, i.e. facing air gaps defined by the spaces between teeth 4a of electrode 4 and teeth 6a of electrode 6. Owing to this configuration, the fluid to be measured, in this case oil, bathes both faces of electrodes 4 and 6 on either side of the plane of the electrodes, such that it can circulate in proximity to teeth 4a and 6a of electrodes 4 and 6.

It will be noted that capacitive element EFM is surrounded by a metal frame CM. This metal frame forms a protective screen as regards external electrical disturbance and thus reduces the influence of such disturbance during measurements. This frame is typically formed by a metal grid.

Substrate 8 is preferably made of a material resistant to temperatures comprised between 20° C. and 200° C. and having a low thermal expansion coefficient, such as a ceramic material. However, it can be made in any other insulating material compatible with the envisaged application of the measuring device. By way of example for a food application that has to be stable within the aforementioned temperature range, substrate 8 could also be made of a fluorinated polymer, such as Teflon.

In order to give an idea, the Applicant carried out conclusive tests with electrodes 4, 6 made of stainless steel having a thickness of the order of 0.8 mm. Electrode 4 comprised 9 teeth and electrode 6 comprised 8 teeth defining 18 air gaps of 100 μm each, the teeth having a width of the order of 1 mm. The substrate was made of ceramic material and had a thickness of the order of 0.6 mm for an external surface of 5×5 cm$^2$.

The capacitance of the capacitive measuring element EFM defined by electrodes 4 and 6 in combination with the oil is measured by processing means 14 comprising for example an analogue capacitance/voltage converter 16 well known to those skilled in the art and associated with a microcontroller 18. By way of example, the capacitance/voltage converter circuit bearing the reference XE2004 marketed by the Xemics company could be used.

Electrodes 4 and 6 are connected to the input of circuit 16, which delivers at output an analogue voltage signal $S_V$ representative of the capacitance of the capacitive measuring element. Signal $S_V$ is supplied to the input of microcontroller 18 that converts signal $S_V$ into a digital signal $S_N$. One could typically use a microcontroller bearing the reference 68HC11 and marketed by the Motorola company. The digital signal at the output of the microcontroller is then supplied to display means 20, made for example in the form of a liquid crystal display or by an LED display. This latter display a digital value representative for example of the dielectric constant of the oil. According to an alternative embodiment, this digital value can be processed in an appropriate manner to indicate the polar compound rate measured in the oil.

Figure 2:
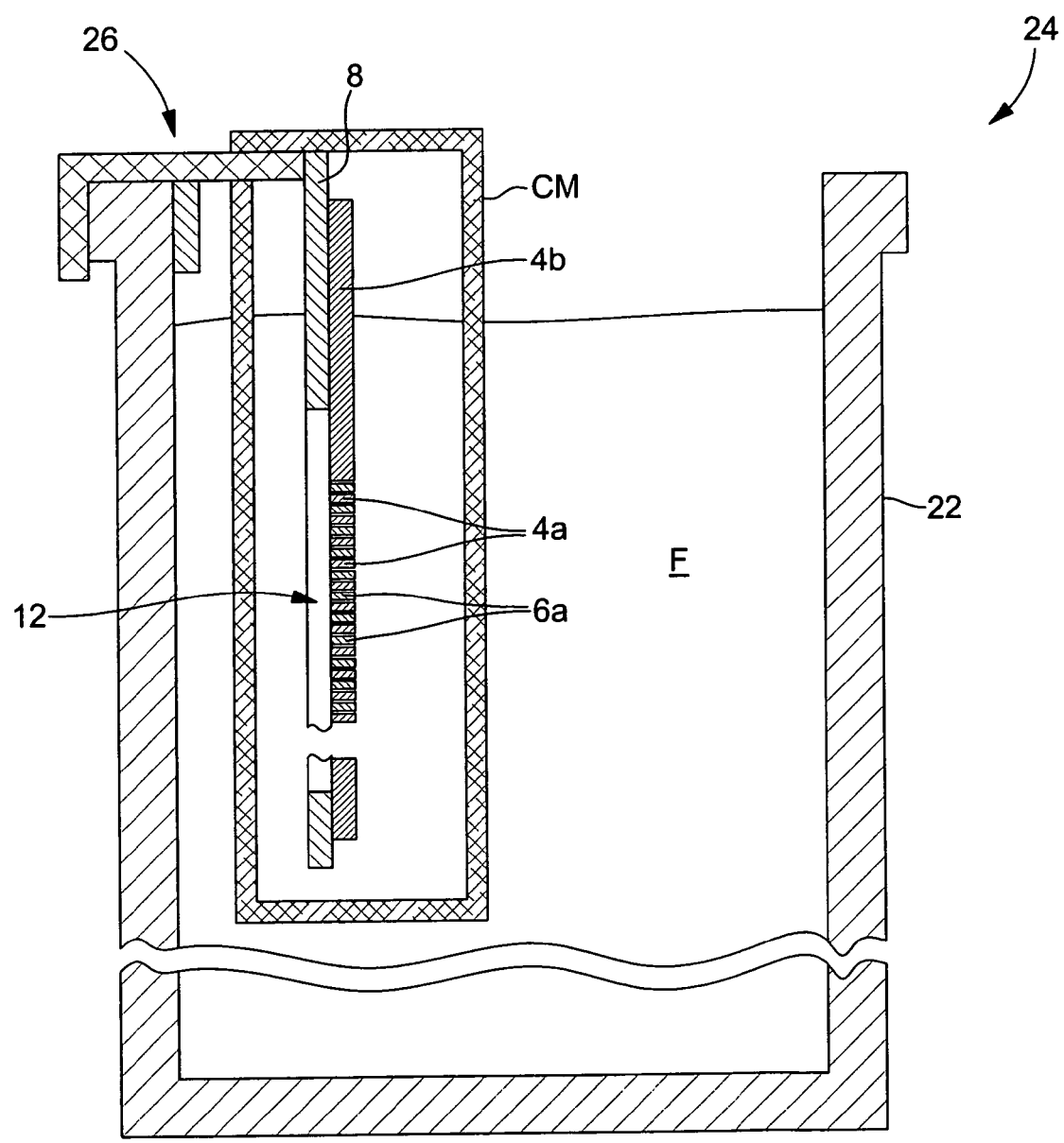
FIG. 2 is a schematic cross-section of a vat of a conventional cooking apparatus to which the measuring device shown in FIG. 1 is fixed, the latter being partially shown in cross-section along the line II-II of FIG. 1 and the processing means having been omitted.

Referring to FIG. 2, one can see how the capacitive measuring element EFM of measuring device 1 is arranged in a vat 22 of a conventional cooking apparatus 24 containing the food oil to be examined. Processing means 14 and display means 20 are omitted from this Figure. These means will be for example arranged in a case associated with the cooking apparatus but separate from vat 22. The cooking apparatus is of course associated with heating means, which are not shown. In this embodiment, the capacitive measuring apparatus is suspended, by hooking means 26 secured to substrate 8, from the top edge of the lateral wall of vat 22 and extending substantially parallel to said wall.

Figure 3:
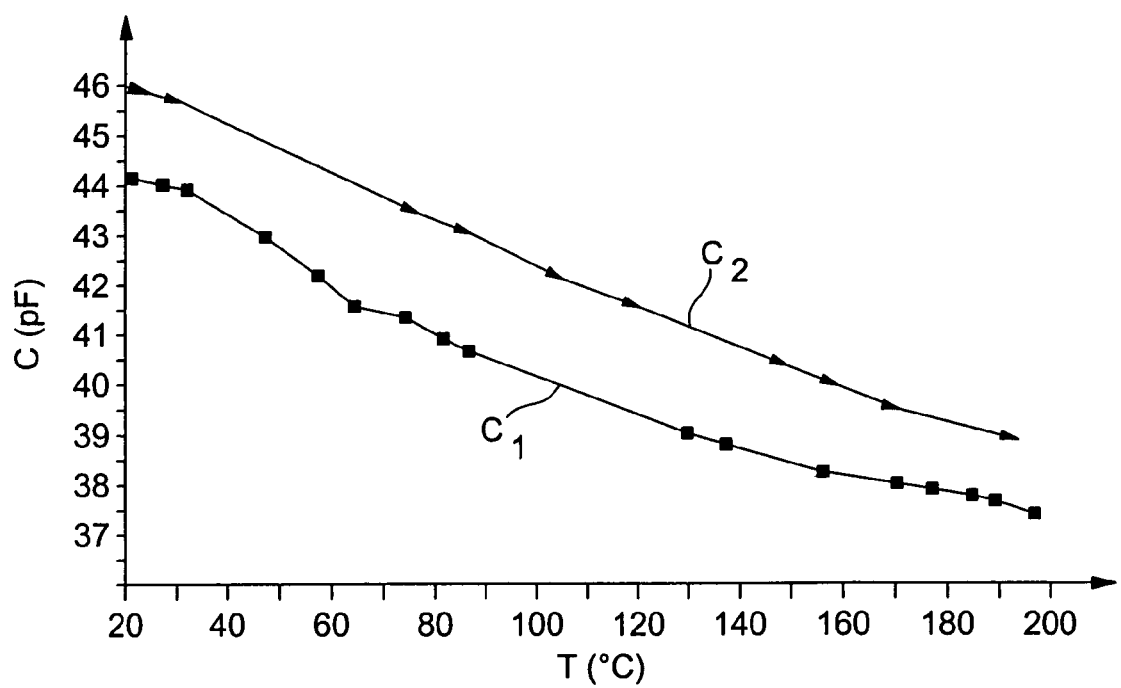
FIG. 3 shows a graph representing, as a function of temperature, the capacitance variation of a capacitive element of the measuring device according to the invention when the capacitive element is immersed in new oil and in used oil.

In FIG. 3, two curves C1 and C2 are shown, respectively illustrating the variation in capacitance C of the capacitive measuring element of device 1 as a function of temperature T for the same oil respectively new and used. "Used oil" means oil that has undergone several cooking cycles. Curve C1 shows the capacitance variation of the capacitive measuring element when electrodes 3 and 4 are immersed in new oil, whereas curve C2 shows the capacitance variation of the capacitive measuring element when electrodes 3 and 4 are immersed in used oil. It will be noted that these two curves generally evolve in the same way as a function of temperature and particularly for a given temperature, the difference between the capacitance measured with a new oil and the used oil is substantially constant. Consequently, the capacitance measurement of the capacitive element EFM easily enables a good oil to be distinguished from used oil within a broad temperature range.

Figure 4:
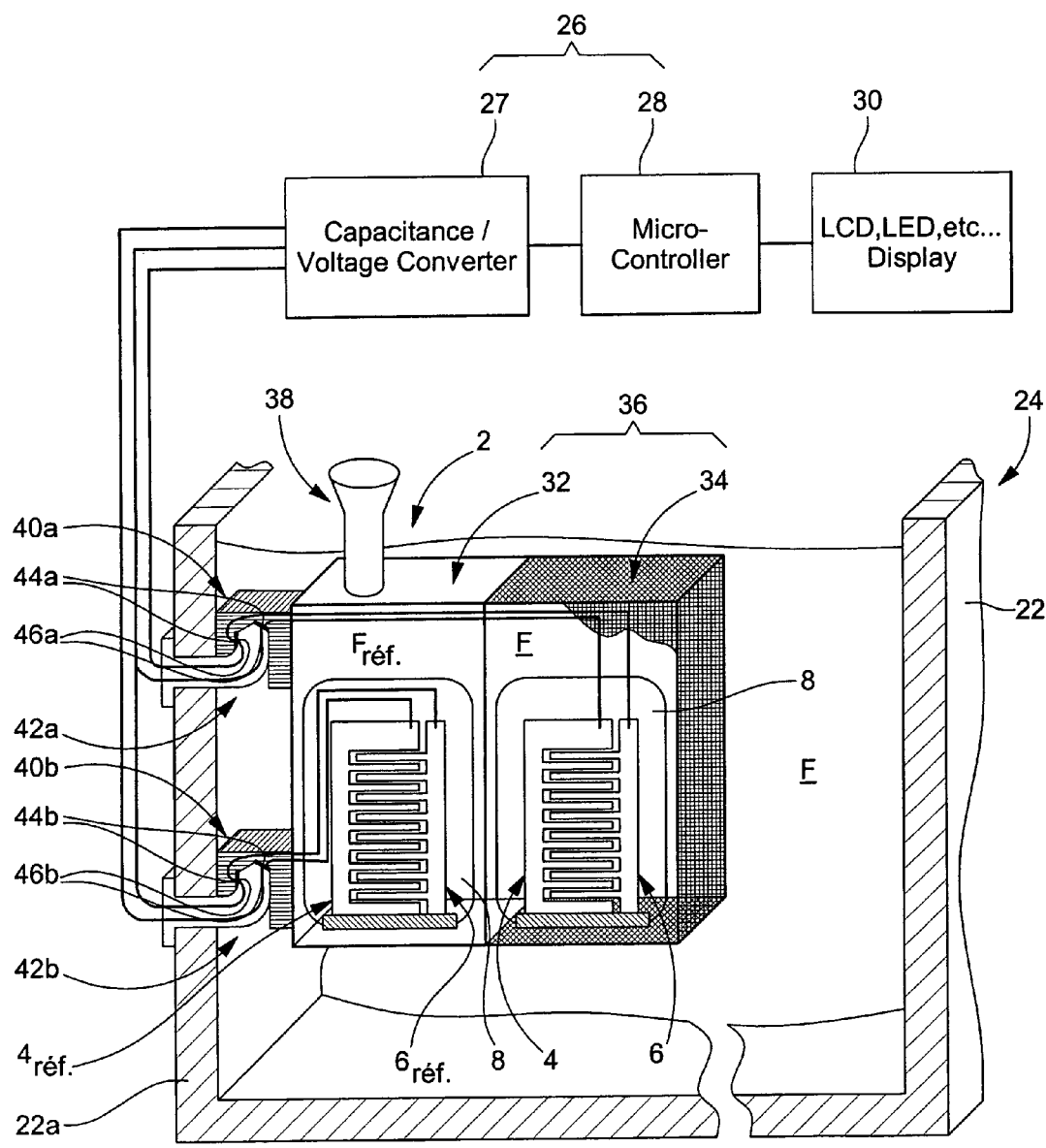
FIG. 4 is a schematic perspective cross-section of a vat of a conventional cooking apparatus to which a measuring device according to a second embodiment of the invention is fixed.

With reference now to FIG. 4, a second embodiment of a measuring device according to the invention can be seen, in which those elements that are identical to those already described are designated by the same reference numerals. This device will also be described within an application to measurement of the quality and/or degradation of a food oil F contained in vat 22 of a cooking apparatus 24.

In this embodiment, sensor 2 comprises, in addition to capacitive measuring element EFM which is immersed in the oil to be measured, a reference capacitive element EFT which is immersed in a reference oil $F_{ref}$ arranged in an enclosed space to be separated from the oil to be measured. The reference oil is oil having the same features as the new oil to be measured. The structure of the reference capacitive element EFR is preferably identical to that of capacitive measuring element EFM although this is not indispensable. Reference capacitive element EFR is thus formed of electrodes $4_{ref}$ and $6_{ref}$ in combination with reference oil $F_{ref}$. Reference capacitive element EFR is thus capable of providing a reference signal representative of the dielectric constant of the reference oil, said signal being able to be compared with the measuring output signal from the capacitive measuring element by processing means 26. The connection of the capacitive measuring element and the reference capacitive element to processing means 26 is schematically shown in FIG. 4. In this example, processing means 26 typically comprise a capacitance/voltage converter 27 with three inputs and one analogue voltage output connected to a microcontroller 28, which is in turn connected to display means 30. A first electrode 6, $4_{ref}$ of each capacitive element EFM and EFR is connected to a first common input of the converter whereas the second electrodes 4, $6_{ref}$ of each capacitive element EFM and EFR are respectively connected to second and third inputs of the capacitance/voltage converter. By way of example, the capacitance/voltage converter 27 bearing the reference XE2004 marketed by the Xemics company can be used and microcontroller 28 is of the same type as that described in conjunction with the first embodiment.

In the embodiment illustrated, the reference capacitive element EFR and the measuring capacitive element EFM are arranged in the vat 22 of cooking apparatus 24. Reference capacitive element EFR is arranged in an enclosed space 32 immersed in the oil to be measured, enclosed space 32 being sealed in a watertight manner such that the reference oil contained therein does not mix with the oil to be measured contained in vat 24. Measuring capacitive element EFM is arranged in an open-worked enclosed space 34, for example whose walls are formed of a grid, such that it is immersed in the oil to be measured. The use of such walls forms a filter that protects the electrodes of measuring capacitive element EFM and thus prevents solid particles suspended in the oil coming into contact with the electrodes, which could interfere with the measurement. Of course, according to another variant, these walls could be omitted.

It will be noted that the walls of enclosed space 32 and the walls of open-worked enclosed space 34 respectively form a protective metal frame or screen against external electrical interference and thereby enable the effect of such interference to be reduced during measurements.

For reasons of convenience, enclosed spaces 32 and 34 are secured to each other and form a single structure 36 that is fixed to vat 22 of cooking apparatus 24. Preferably and as illustrated in FIG. 4, the capacitive elements are fixed in their respective enclosed space by insulating supports cooperating with their substrate.

It will be noted that enclosed space 32 containing the reference oil comprises a filling channel 38, the orifice of which can be sealed in a watertight manner by a cap or a lid (not shown). According to a variant that is not shown, enclosed space 32 can further comprise drainage means arranged in its bottom part.

It will also be noted that structure 36 is advantageously arranged in proximity to an inner vertical wall 22a of the vat, which leaves sufficient space free for cooking food while the measurements are carried out.

Structure 36 further comprises on one of its lateral walls, hooking means 40a, 40b for cooperating with complementary hooking means 42a, 42b secured to wall 22a. In the example illustrated, hooking means 40 and complementary hooking means 42 respectively comprise two hooks 40a, 40b, 42a and 42b cooperating in pairs. Structure 36 can also be suspended in a removable manner inside vat 22. It will be noted that this removable assembly of structure 36 facilitates the filling and drainage of enclosed space 32 as well as maintenance operations for capacitive elements EFM and EFR. Moreover, since structure 36 is of simple construction and in particular, does not comprise any moving mechanical parts, it is extremely reliable.

In this embodiment, the electrical connections between the two capacitive elements and processing means 26 arranged outside the vat occur via hooks 40a, 40b, 42a and 42b. Thus hooks 40a, 40b comprises complementary contact pads 44a, 44b respectively connected to capacitive elements EFM and EFR. Hooks 42a and 42b comprise complementary contact pads 46a, 46b connected to processing means 26 and intended to come into contact with contact pads 44a, 44b when structure 26 is suspended in the vat. The electrical connection between contact pads 44a, 44b and the capacitive elements is achieved by wires passing, in a watertight manner, through the wall of enclosed space 32. Likewise, the electrical connection between pads 46a, 46b and the processing means is achieved by wires passing, in a watertight manner, through the wall of vat 22. Of course, according to a variant, the various connections between the capacitive elements and the processing circuit can be independent of the suspension means in vat 22, directly connected to a separate case that may or may not comprise display means 30 and forming, with structure 36, a portable measuring unit independent of any cooking apparatus.

Figure 5:
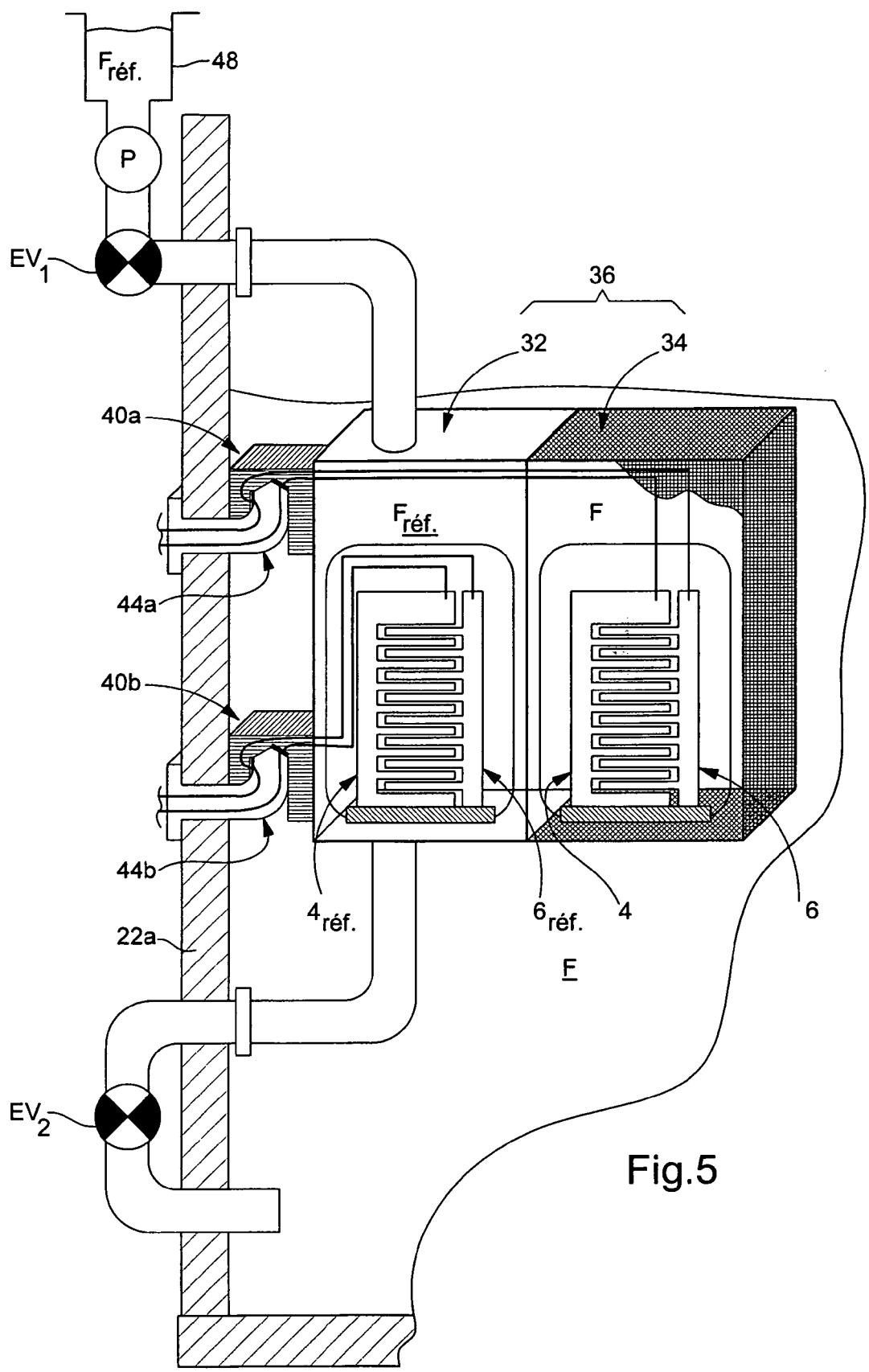
FIG. 5 shows a variant of the second embodiment of the measuring device according to the invention.

FIG. 5 shows a variant of the second embodiment of the measuring device according to the invention, wherein the device is associated with a system for renewing the reference oil. The renewal system comprises a container 48 containing new oil and arranged outside vat 22. Container 48 is connected to an inlet orifice of enclosed space 32 by a pipe on which are placed a pump P and a solenoid valve EV1. Enclosed space 32 is connected, via an outlet orifice, to a pipe provided with a solenoid valve EV2 and opening into vat 22. The used reference oil can thus be reinjected into vat 22 and reused.

It will be noted that pump P and the two solenoid valves EV1 and EV2 are preferably placed outside vat 22 to protect them against the effects of temperature.

It will also be noted that the pump could be omitted in variants wherein container 48 is placed high enough that the oil to be measured does not rise up into the enclosed space containing the reference oil when the solenoid valves are open.

This renewal system can advantageously be associated with means for automatically programmed means for controlling the pump and the solenoid valves. These means can typically take the form of a microprocessor. This type of system facilitates use of the measuring device.

Figure 6:
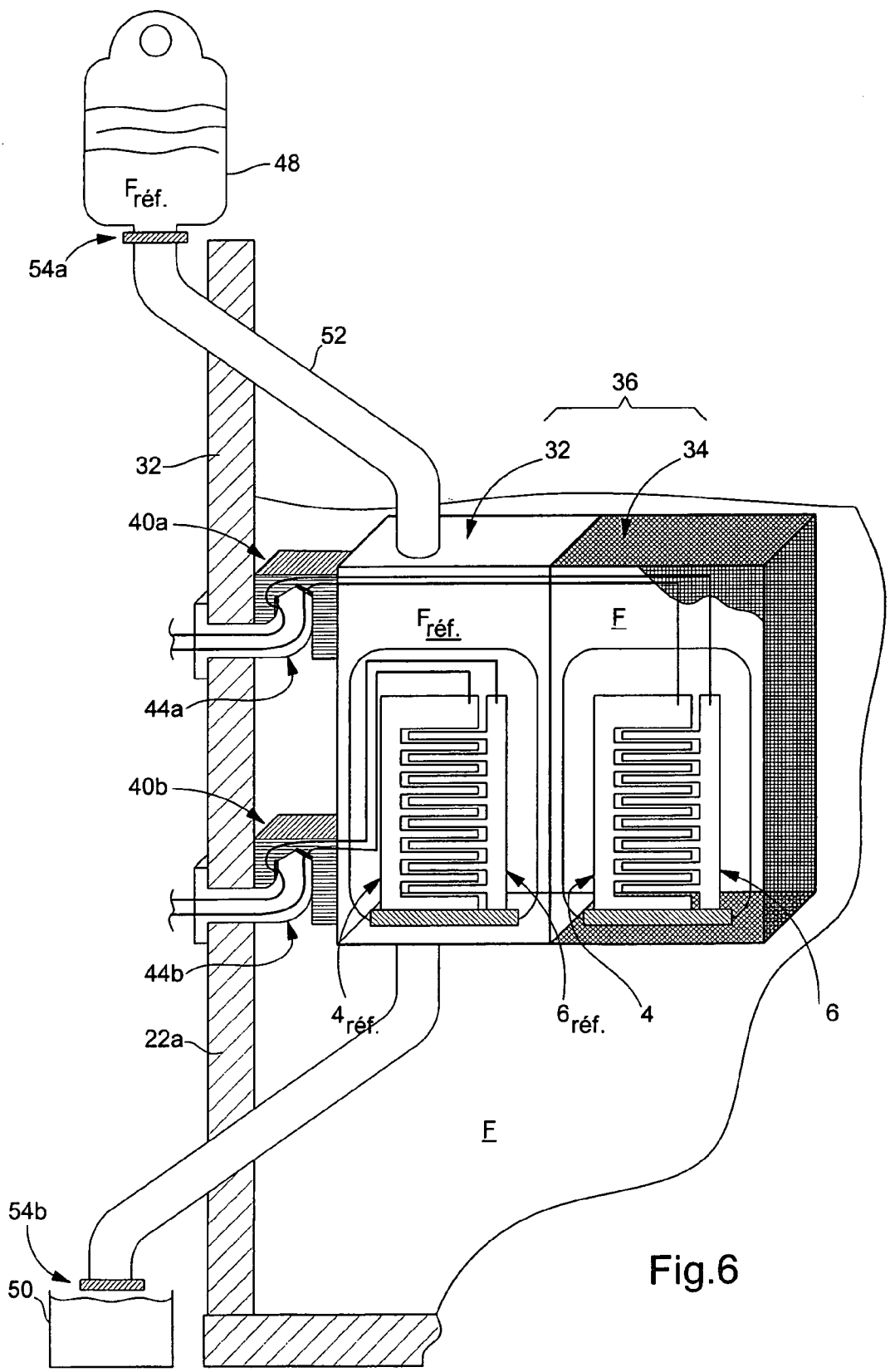
FIG. 6 shows a variant of the embodiment illustrated in FIG. 5.

FIG. 6 shows a variant of the embodiment illustrated in FIG. 5 wherein container 48 is directly connected to an inlet orifice of enclosed space 32 by a pipe 52. Enclosed space 32 is connected by an outlet orifice to a pipe passing through one wall of vat 22 and opening out into a recovery tank 50 arranged outside vat 22. Container 48 is preferably formed of a watertight pouch connected to pipe 52 by a drip type flow control device 54a and the outlet orifice of enclosed space 32 is also associated with a flow control device 54b of the same type. Of course, the flow rate of the two flow control devices are identical and can advantageously be adjusted so that the volume of enclosed space 32 is renewed daily. Another advantage of this embodiment is that the reference oil is permanently sheltered from oxygen.

The advantage of this variant lies in the fact that it does not comprise any moving mechanical parts, which improves its reliability and facilitates maintenance.

With the measuring device according to the second embodiment, the reference capacitive element, which is immersed in the new oil at substantially the same temperature as the oil to be measured, in which the measuring capacitive element is arranged, enables, by a Wheatstone bridge arrangement of the two capacitive elements, variations in the dielectric constant of these elements, caused by degradation of the oil, to be distinguished from variants caused by temperature fluctuations. This type of bridge arrangement is described, for example, in the article entitled, "Application of capacitance techniques in sensor design" by Willem Chr. Heerens published in J. Phys. E: Scientific Instruments 19: 897 906 (1986), which is incorporated in this Application by reference.

It will be understood that various modifications and/or improvements evident to those skilled in the art can be made to the embodiment described in the present description without departing from the scope of the present invention defined by the annexed claims. In particular, one could envisage arranging the capacitive elements in any orientation in the vat containing the fluid to be measured.

Figure 7:
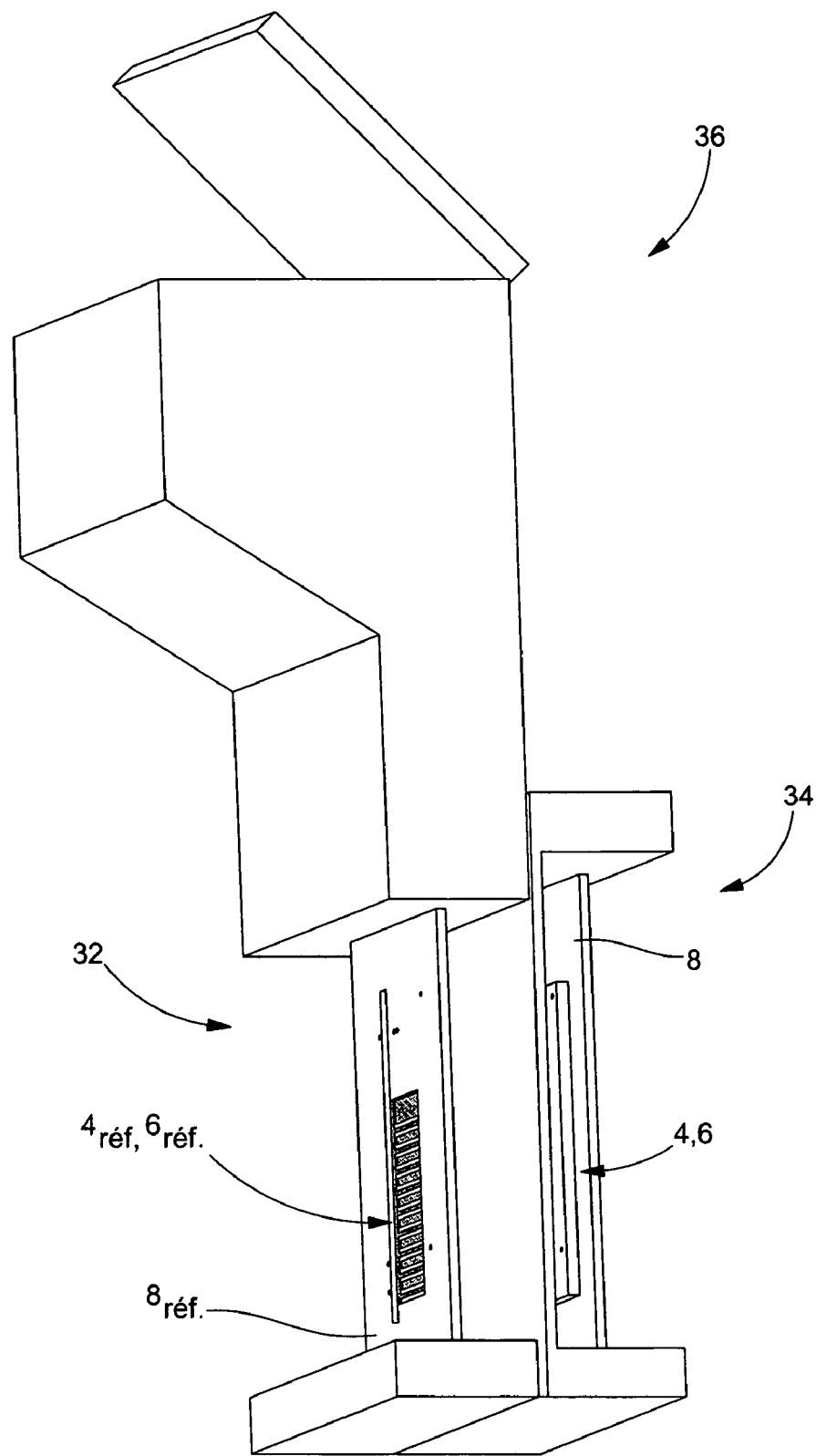
FIG. 7 shows an example embodiment of a support structure for the capacitive elements of the device of the invention.

One could also envisage making single structure 36 in accordance with the configuration illustrated in FIG. 7 wherein the enclosed spaces 32 and 34 are arranged in a more compact manner, the walls of the enclosed spaces having been omitted in order to show capacitive elements EFM and EFR.

One could also envisage, in the second embodiment, having an electrode common to both capacitive elements in order to limit the number of connections.

It goes without saying that the measuring device according to the invention that has just been described is not limited to an application for measuring food oils and could be used for measuring the quality and/or degradation of any fluid wherein the evolution of the dielectric constant is representative of its quality and/or degradation.

The invention claimed is:

1. Cooking apparatus including a vat for containing a cooking fluid and heating means, wherein it further includes a device for measuring the quality and/or degradation of said cooking fluid, said measuring device including a sensor having at least one pair of electrodes spaced apart from each other and extending in substantially the same plane, each electrode of each pair of electrodes further having the shape of a comb having a plurality of substantially parallel teeth, the teeth of one of the electrodes being interdigitated with the teeth of the other electrode, the electrodes and said cooking fluid forming a measuring capacitive element whose capacitance varies as a function of the dielectric constant of the fluid, said sensor being capable of providing an electrical output signal representative of said dielectric constant, and processing means for receiving said output signal and determining the degree of quality and/or degradation of said cooking fluid on the basis of said output signal, the measuring capacitive element being arranged in said vat such that both sides of its electrodes are immersed in the cooking fluid on either side of said plane of the electrodes so that said cooking fluid can flow passing through said plane, wherein the sensor further includes a reference capacitive element, including at least one pair of electrodes spaced apart from each other to be immersed in a reference fluid, the electrodes and the reference fluid forming a measuring capacitive element whose capacitance varies as a function of the dielectric constant of the reference fluid, said sensor being capable of providing an electrical output signal representative of said reference dielectric constant to said processing means and wherein the processing means are arranged for comparing the output signal to the reference signal, wherein the reference fluid is arranged in an enclosed space insulated from the cooking fluid to be measured and in thermal contact with the latter, such that the reference fluid has substantially the same temperature as the cooking fluid to be measured, wherein the enclosed space containing the reference fluid is associated with a system for renewing said reference fluid, and wherein said renewal system includes a reference fluid tank in communication with said enclosed space and wherein said system includes flow control means to allow regular renewal of the reference fluid contained in said enclosed space.

2. A method of measuring the quality and/or the degradation of a food oil, said method comprising the steps of:

immersing a sensor in said oil to be measured, said sensor comprising at least one pair of electrodes spaced apart from each other and extending in substantially the same plane, each electrode of each pair of electrodes further having the shape of a comb having a plurality of substantially parallel teeth, the teeth of one of the electrodes being interdigited with the teeth of the other electrode, the electrodes and said oil forming a measuring capacitive element whose capacitance varies as a function of the dielectric constant of the oil, said sensor providing an electrical output signal representative of said dielectric constant;

receiving said output signal and determining the degree of quality and/or degradation of said oil on the basis of said output signal;

immersing both sides of the electrodes in the oil, on either side of said plane, such that said oil can flow passing through said plane, said method further comprising the step of providing the sensor with a reference capacitive element comprising at least one pair of reference electrodes spaced apart from one another, said reference capacitive element being intended to be immersed in a reference oil, the reference electrodes and the reference fluid forming a reference capacitive element whose capacitance varies as a function of the dielectric constant of the reference oil, said reference capacitive element being capable of providing a reference signal representative of said reference dielectric constant to said processing means, and wherein the processing means are arranged for comparing the output signal to the reference signal, wherein the reference fluid is arranged in an enclosed space insulated from said oil to be measured and in thermal contact with the latter, such that the reference oil has substantially the same temperature as said oil to be measured, wherein the enclosed space containing the reference oil is associated with a system for renewing said reference oil, and wherein said renewal system comprises a reference oil tank in communication with said enclosed space and wherein said system comprises flow control means so as to allow regular renewal of the reference oil contained in said enclosed space.

* * * * *